United States Patent
Haerinia et al.

(10) Patent No.: US 11,303,160 B2
(45) Date of Patent: Apr. 12, 2022

(54) WIRELESS POWER TRANSFER AND WIRELESS COMMUNICATIONS BETWEEN TWO ELECTRONIC COMPONENTS

(71) Applicants: Mohammad Haerinia, Lowell, MA (US); Sima Noghanian, Poway, CA (US); Reem Shadid, Amman (JO)

(72) Inventors: Mohammad Haerinia, Lowell, MA (US); Sima Noghanian, Poway, CA (US); Reem Shadid, Amman (JO)

(73) Assignee: THE UNIVERSITY OF NORTH DAKOTA, Grand Forks, ND (US)

( * ) Notice: Subject to any disclaimer, the term of this patent is extended or adjusted under 35 U.S.C. 154(b) by 7 days.

(21) Appl. No.: 16/886,195

(22) Filed: May 28, 2020

(65) Prior Publication Data

US 2020/0381956 A1 Dec. 3, 2020

Related U.S. Application Data

(60) Provisional application No. 62/853,216, filed on May 28, 2019.

(51) Int. Cl.
*H02J 50/40* (2016.01)
*H02J 50/10* (2016.01)
(Continued)

(52) U.S. Cl.
CPC .............. *H02J 50/40* (2016.02); *A61N 1/362* (2013.01); *A61N 1/3787* (2013.01);
(Continued)

(58) Field of Classification Search
CPC .. H02J 50/40; H02J 50/10; H02J 50/27; H02J 7/0045; H02J 50/23; H02J 7/02;
(Continued)

(56) References Cited

U.S. PATENT DOCUMENTS 9,812,790 B2 * 11/2017 Lavedas .................. H01Q 7/02
10,396,859 B1 * 8/2019 Hong .................. H04B 17/318
(Continued)

*Primary Examiner* — Daniel Cavallari
*Assistant Examiner* — Brian K Baxter
(74) *Attorney, Agent, or Firm* — Kinney & Lange, P.A.

(57) ABSTRACT

Apparatus and associated methods relate to providing wireless power transfer and wireless communications between two electronic components, each having an inductive coil and a microwave antenna centered about a common central axis, thereby ensuring alignment with one another. Wireless power transfer can be performed using electromagnetic coupling between the inductive coils and/or the microwave antennae of the two electronic components. In some embodiments, the two electronic components are an implantable biomedical device and an external interface system for the implantable biomedical device. Power-receive and power-transmit controllers control operation of power transmission by the external interface system and power reception by the implantable biomedical device, respectively. In some embodiments, the microwave antenna has a resonance frequency that is configured by location of an electrical connection to a ground plane. A communication controller can be configured to control the resonance frequency of the microwave antenna by controlling a switch network.

20 Claims, 6 Drawing Sheets

(51) Int. Cl.
- *H02J 50/27* (2016.01)
- *H02J 7/00* (2006.01)
- *H02J 50/23* (2016.01)
- *H01Q 1/38* (2006.01)
- *H01F 38/14* (2006.01)
- *A61N 1/362* (2006.01)
- *A61N 1/372* (2006.01)
- *A61N 1/378* (2006.01)
- *H02J 7/02* (2016.01)

(52) U.S. Cl.
CPC ......... *A61N 1/37229* (2013.01); *H01F 38/14* (2013.01); *H01Q 1/38* (2013.01); *H02J 7/0045* (2013.01); *H02J 7/02* (2013.01); *H02J 50/10* (2016.02); *H02J 50/23* (2016.02); *H02J 50/27* (2016.02)

(58) Field of Classification Search
CPC .......... H01Q 1/38; H01F 38/14; A61N 1/362; A61N 1/37229; A61N 1/3787

See application file for complete search history.

(56) References Cited

U.S. PATENT DOCUMENTS

| | | | |
|---|---|---|---|
| 10,790,711 B2* | 9/2020 | Kim | H02J 50/40 |
| 2008/0252254 A1* | 10/2008 | Osada | H02J 7/00714 320/108 |
| 2009/0160718 A1* | 6/2009 | Yen | H01Q 15/10 343/742 |
| 2013/0335020 A1* | 12/2013 | Moore | H02J 50/90 320/109 |
| 2014/0117927 A1* | 5/2014 | Chateau | H01Q 1/2225 320/108 |
| 2016/0345125 A1* | 11/2016 | Kim | H04B 5/0087 |
| 2016/0359370 A1* | 12/2016 | Park | H02J 7/00308 |
| 2017/0040107 A1* | 2/2017 | Peralta | H02J 7/025 |
| 2017/0040688 A1* | 2/2017 | Peralta | H01Q 1/526 |
| 2017/0040694 A1* | 2/2017 | Singh | H02J 50/12 |
| 2017/0040696 A1* | 2/2017 | Peralta | H02J 50/12 |
| 2017/0054213 A1* | 2/2017 | Singh | H04B 5/0087 |
| 2017/0141465 A1* | 5/2017 | Sharawi | H01Q 21/28 |
| 2017/0302086 A1* | 10/2017 | Kwan | H02J 50/12 |
| 2017/0373522 A1* | 12/2017 | Pelosi | H02J 7/0021 |
| 2018/0109146 A1* | 4/2018 | Meng | H04B 5/0093 |
| 2018/0263557 A1* | 9/2018 | Kahlman | H02J 50/10 |
| 2018/0278099 A1* | 9/2018 | Hong | H02J 7/025 |
| 2019/0288567 A1* | 9/2019 | Kabiri | H01Q 7/00 |
| 2019/0308514 A1* | 10/2019 | Parimi | H02J 50/12 |
| 2020/0403454 A1* | 12/2020 | Chen | H02J 50/12 |

\* cited by examiner

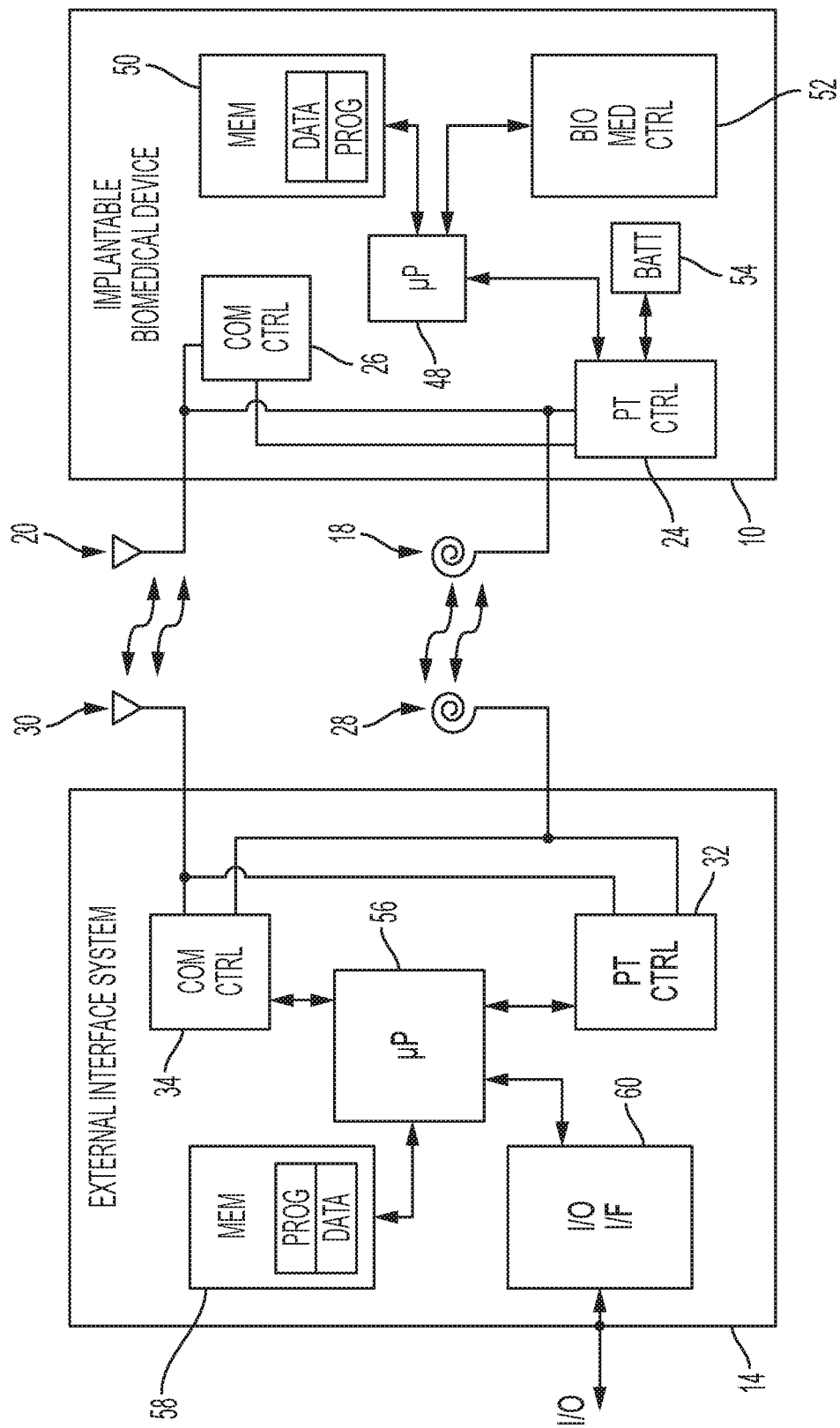

WIRELESS POWER TRANSFER AND WIRELESS COMMUNICATIONS BETWEEN TWO ELECTRONIC COMPONENTS

CROSS-REFERENCE TO RELATED APPLICATION(S)

This application claims the benefit of U.S. Provisional Application No. 62/853,216 filed May 28, 2019, titled "Hybrid Inductive-based Power Transfer and Wireless Antenna System for Biomedical Implanted Devices," by Mohammad Haerinia, Sima Noghanian, and Reem Shadid, the entire disclosure of which is hereby incorporated by reference.

BACKGROUND

Implantable biomedical devices are widely used in various biomedical applications. Many of these implantable biomedical devices rely on electrical power to perform their functions. Batteries commonly are used to supply such electrical power. Battery life, however, can be short in comparison to the required lifetime of the implantable biomedical device. If a battery of an implanted biomedical device is in need of replacement, a surgical procedure must be performed on the patient in whom the biomedical device is implanted. Thus, non-surgical means for providing electrical power to implanted biomedical devices are needed.

Furthermore, the functions of implanted biomedical devices often can be facilitated by communication with interface systems external to the patient. For example, such communication could facilitate various operations, such as: software upgrades and/or programming of implanted biomedical devices; biomedical data collection of biomedical data obtained by implanted biomedical devices; device data collection of implanted biomedical devices, etc. Thus, non-invasive means of communicating with implanted biomedical devices are needed.

Both power transfer and communications are operations that need to be performed regardless of the location of the implanted biomedical devices. Some implanted biomedical devices are implanted at shallow depths beneath a skin surface of a patient, and other implanted biomedical devices are implanted at larger depths beneath the skin surface of patients. Furthermore, some implanted devices can migrate within a patient over time. For example, patients can gain or lose weight, changing the depth at which an implanted device resides, or the implanted device can migrate in response to normal physical activity of the patient. Thus, there is a need for power transfer and communications systems to be operable over different and/or changing locations of implanted biomedical devices.

SUMMARY

Apparatus and associated methods relate to a dual-channel electronic device including and inductive coil, a power-receive controller, a microwave antenna, and a communications controller. Both the inductive coil and the microwave antenna are centered about a central axis. The power-receive controller is configured to provide regulated power to the dual-channel electronic device using electrical energy coupled into the inductive coil by an interface system for the dual-channel electronic device. The communications controller is configured to facilitate communications between the dual-channel electronic device and the interface system for the dual-channel electronic device.

Some embodiments relate to an external interface system for a dual-channel electronic device. The external interface includes and inductive coil, a power-transmit controller, a microwave antenna, and a communications controller. Both the inductive coil and the microwave antenna are centered about a central axis. The power-transmit controller is configured to excite the inductive coil so as to transmit wireless power to the dual-channel electronic device. The communications controller is configured to facilitate communications between the dual-channel electronic device and the interface system for the dual-channel electronic device.

Some embodiments relate to a method for supplying energy to a dual-channel electronic device. The method includes determining a separation distance between the dual-channel electronic device and an interface system for providing wireless power transfer to the dual-channel electronic device. The method includes comparing the separation distance determined with a critical separation distance. The method includes selecting, based on the comparison of the separation distance with the critical separation distance, an inductive coil or a microwave antenna for provision of wireless power transfer. The method also includes providing wireless power transfer to the dual-channel electronic device using the inductive coil or the microwave antenna selected.

BRIEF DESCRIPTION OF THE DRAWINGS

FIGS. 5A-5B are block diagrams of the implantable device and the interface for the implantable device, respectively.

DETAILED DESCRIPTION

Apparatus and associated methods relate to providing wireless power transfer and wireless communications between two electronic components, each having an inductive coil and a microwave antenna centered about a common central axis, thereby ensuring alignment with one another. Wireless power transfer can be performed using electromagnetic coupling between the inductive coils and/or the microwave antennae of the two electronic components. In some embodiments, the two electronic components are an implantable biomedical device and an external interface system for the implantable biomedical device. Power-receive and power-transmit controllers control operation of power transmission by the external interface system and power reception by the implantable biomedical device, respectively. In some embodiments, the microwave antenna has a resonance frequency that is configured by location of an electrical connection to a ground plane. A communication controller can be configured to control the resonance frequency of the microwave antenna by controlling a switch network.

Figure 1:
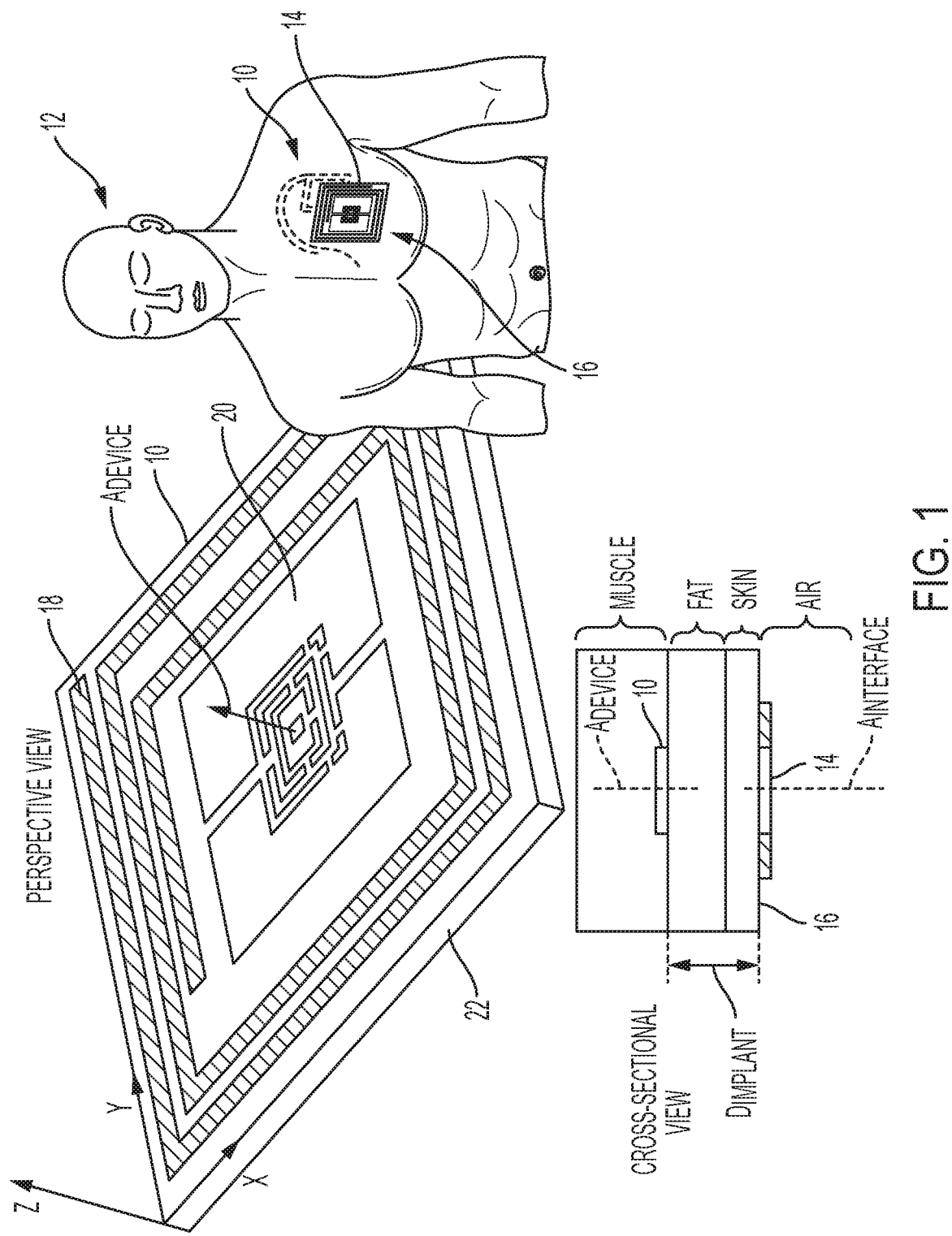
FIG. 1 is a schematic diagram of a patient with an implantable biomedical device that is in communication with an external interface system for the implanted device.

FIG. 1 is a schematic diagram of a patient with an implantable biomedical device that is in communication with an external interface system for the implantable device. In FIG. 1, Implantable biomedical device 10 (shown in phantom) has been implantable into patient 12. External interface system 14 is proximate skin surface 16 of patient 12 so as to be aligned with implantable medical device 10. External interface system 14 is aligned so as to transmit wireless power to implantable medical device 10 as well as communicate with implantable medical device 10. External interface system can be adhesively affixed to skin surface 16 of patient 12 or otherwise held in place on skin surface 16 of patient 12. In the depicted embodiment, implantable medical device 10 is a cardiac pacemaker, but various other implantable medical devices can be equipped with wireless power transfer and communication systems as will be described below. Moreover, other (e.g., non-implantable and/or non-biomedical devices) can also be equipped with such wireless power transfer and communications systems.

Implantable biomedical device 10 has inductive coil 18 and microwave antenna 20 for receiving wireless power transfer and communications from external interface system 14 for implantable biomedical device 10. In the depicted embodiment, inductive coil 18 and microwave antenna 20 are microstrip type features formed upon insulative substrate 22. Inductive coil 18 and microwave antenna 20 have geometric arrangements in the X-Y plane that can be formed using photolithographic techniques, for example. Inductive coil 18 and microwave antenna 20 are both centered about central axis $A_{DEVICE}$, which is an axis in the Z-direction. Inductive coil 18 circumscribes microwave antenna 20. External interface system 14 has a similar configuration of an inductive coil and a microwave antenna.

Implantable biomedical device 10 has been implanted within patient 12 at a distance $D_{IMPLANT}$ beneath skin surface 16 of patient 12. External interface system 14 has been placed proximate skin surface 16 and aligned with implantable biomedical device 10 so as to provide wireless power transfer to and communicate with implantable biomedical device 10. External interface system 14 has an inductive coil and a microwave antenna both aligned about a central axis $A_{INTERFACE}$. External interface system 14 can be aligned with implantable biomedical device 10 by translating external interface system 14 along skin surface 16 until central axis $A_{INTERFACE}$ of external interface system 14 is colinear with central axis $A_{DEVICE}$ of implantable biomedical device 10. Such alignment can maximize the electromagnetic coupling between both the inductive coils and the microwave antennae of implantable biomedical device 10 and external interface system 14. Such simultaneous alignment of both the inductive coils and the microwave antennae of implantable biomedical device 10 and external interface system 14 can facilitate simultaneous wireless power transfer and wireless communications.

When external interface system 14 is substantially aligned with implantable biomedical device 10, wireless power transfer and communications can be performed. Communications between external interface system 14 and implantable biomedical device 10 can be performed via the microwave antennae of external interface system 14 and implantable biomedical device 10. For example, external interface system 14 can transmit configuration data and/or commands to implantable biomedical device 10, and/or receive biomedical data acquired by or device data of implantable biomedical device 10. In some embodiments, resonance frequencies of the microwave antennae can be configurable such that the communications are performed at a selectable frequency as will be detailed below. Communications between external interface system 14 and implantable biomedical device 10 can be controlled by communications controllers of external interface system 14 and implantable biomedical device 10, as will be described below.

Electrical power can be transmitted wirelessly from external interface system 14 to implantable biomedical device 10 via the inductive coils of external interface system 14 and implantable biomedical device 10. Electrical power also can be transmitted wirelessly from external interface system 14 to implantable biomedical device 10 via the microwave antennae of external interface system 14 and implantable biomedical device 10. The efficacy of wireless power transfer using the inductive coil and/or the microwave antenna can be a function of various parameters, such as, for example, distance $D_{IMPLANT}$ beneath skin surface 16 of patient 12, misalignment $\Delta A$ of central axes $A_{INTERFACE}$ and $A_{DEVICE}$, battery charge state of a battery of implantable biomedical device 10, etc. Power-receive and power-transmit controllers can be configured to control operation of power transmission by external interface system 18 and power reception by implantable biomedical device 10, respectively, as will be detailed below.

Although the FIG. 1 embodiment is an implantable biomedical device, various other dual-channel electronic devices can be configured to provide wireless power transfer and communications between a dual-channel electronic device and an interface system for the dual-channel electronic device. Any dual-channel electronic device having an inductive coil aligned to and circumscribing a microwave antenna can avail itself of the capabilities of the system that will be described below.

Figure 2B:
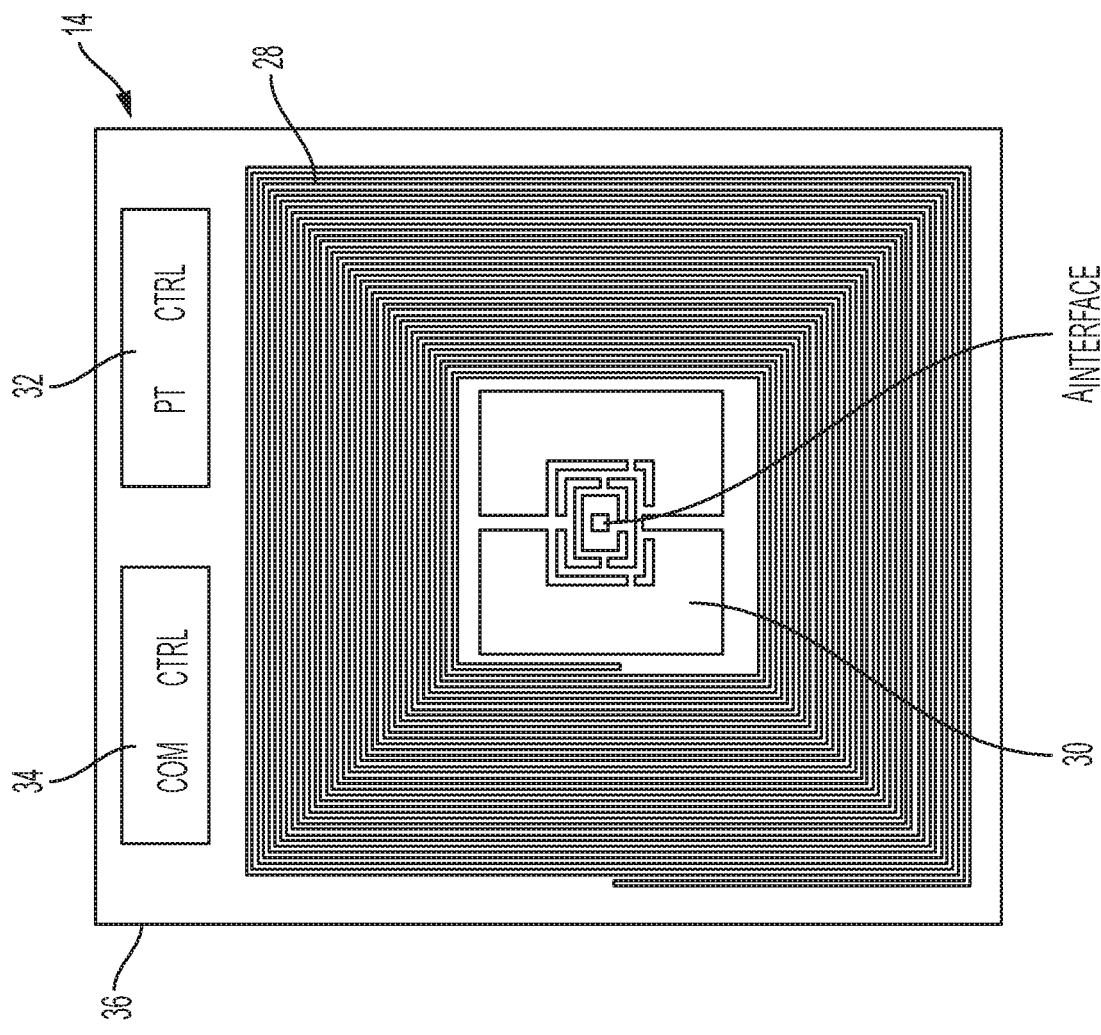
FIGS. 2A-2B are plan views showing an embodiment of inductive coils and microwave antennae for an implantable biomedical device and an external interface system for the implantable biomedical device, respectively.
Figure 2A:
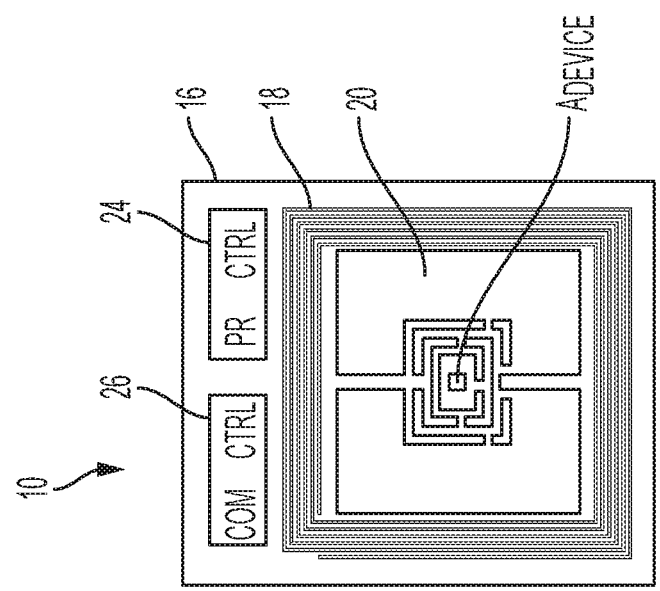

FIGS. 2A-2B are plan views showing an embodiment of inductive coils and microwave antennae for an implantable biomedical device and an external interface system for the implantable biomedical device, respectively. In FIG. 2A, implantable biomedical device 10 includes inductive coil 18, microwave antenna 20, power-receive controller 24, and communications controller 26. In the depicted embodiment, inductive coil 18 is a microstrip type of structure that has been formed on insulative substrate 16. Similarly, microwave antenna 20 is also of the microstrip type of structure that has been formed on insulative substrate 16. Both inductive coil 18 and microwave antenna 20 are centered about central axis $A_{DEVICE}$, such that inductive coil 18 circumscribes microwave antenna 20. Power-receive controller 24 is configured to provide regulated power to biomedical implantable device 10 using electrical energy coupled into the inductive coil by external interface system 14 for biomedical implantable device 10. Communications controller 26 is configured to facilitate communications between biomedical implantable device 10 and external interface system 14 for biomedical implantable device 10.

In FIG. 2B, external interface system 14 includes inductive coil 28, microwave antenna 30, power-transmit controller 32, and communications controller 34. In the depicted embodiment, inductive coil 28 is a microstrip type of structure that has been formed on insulative substrate 36. Similarly, microwave antenna 30 is also of the microstrip type of structure that has been formed on insulative substrate 36. Both inductive coil 28 and microwave antenna 30 are centered about central axis $A_{INTERFACE}$, such that inductive coil 28 circumscribes microwave antenna 30. Power-receive controller 32 is configured to provide an AC current signal in inductive coil 28 so as to excite inductive coil 28 and to transmit wireless power to biomedical implantable device 10. Communications controller 34 is configured to facilitate communications between biomedical implantable device 10 and external interface system 14 for biomedical implantable device 10.

Inductive coils 18 and 28 can be used for providing wireless power transfer from external interface system 14 to implantable biomedical device 10. Such wireless power transfer has a power transfer efficiency that is a function of the distance and/or tissue between external interface system 14 and implantable biomedical device 10. In general, the efficiency of such power transfer decreases with increasing depth $D_{IMPLANT}$ at which implantable biomedical device is implanted. In a similar fashion, a power transfer efficiency of communication between microwave antennae 20 and 30 is also a function of distance and/or tissue between external interface system 14 and implantable biomedical device 10. In general, the efficiency of such power transfer decreases with increasing depth $D_{IMPLANT}$ at which implantable biomedical device is implanted. Because inductive coils 18 and 28 are configured to operate at frequencies that are much less than those frequencies at which microwave antennae 20 and 30 are configured to operate, the power transfer efficiency/depth relations of these different wireless systems are different.

For example, there can be some combinations of depth locations $D_{IMPLANT}$ and intervening tissue compositions for which power transfer efficiency is greatest when using inductive coils 18 and 28, and other combinations of depth locations $D_{IMPLANT}$ and intervening tissue compositions for which power transfer efficiency is greatest when using microwave antennae 20 and 30. Wireless power transfer can use inductive coils 18 and 28 to perform wireless power transform when implanted biomedical device is situated at a bodily location where efficiency of such wireless power transfer favors inductive coils 18 and 28. Wireless power transfer can use microwave antennae 20 and 30 to perform wireless power transform when implanted biomedical device is situated at other bodily locations where efficiency of such wireless power transfer favors microwave antennae 20 and 30.

Figure 3:
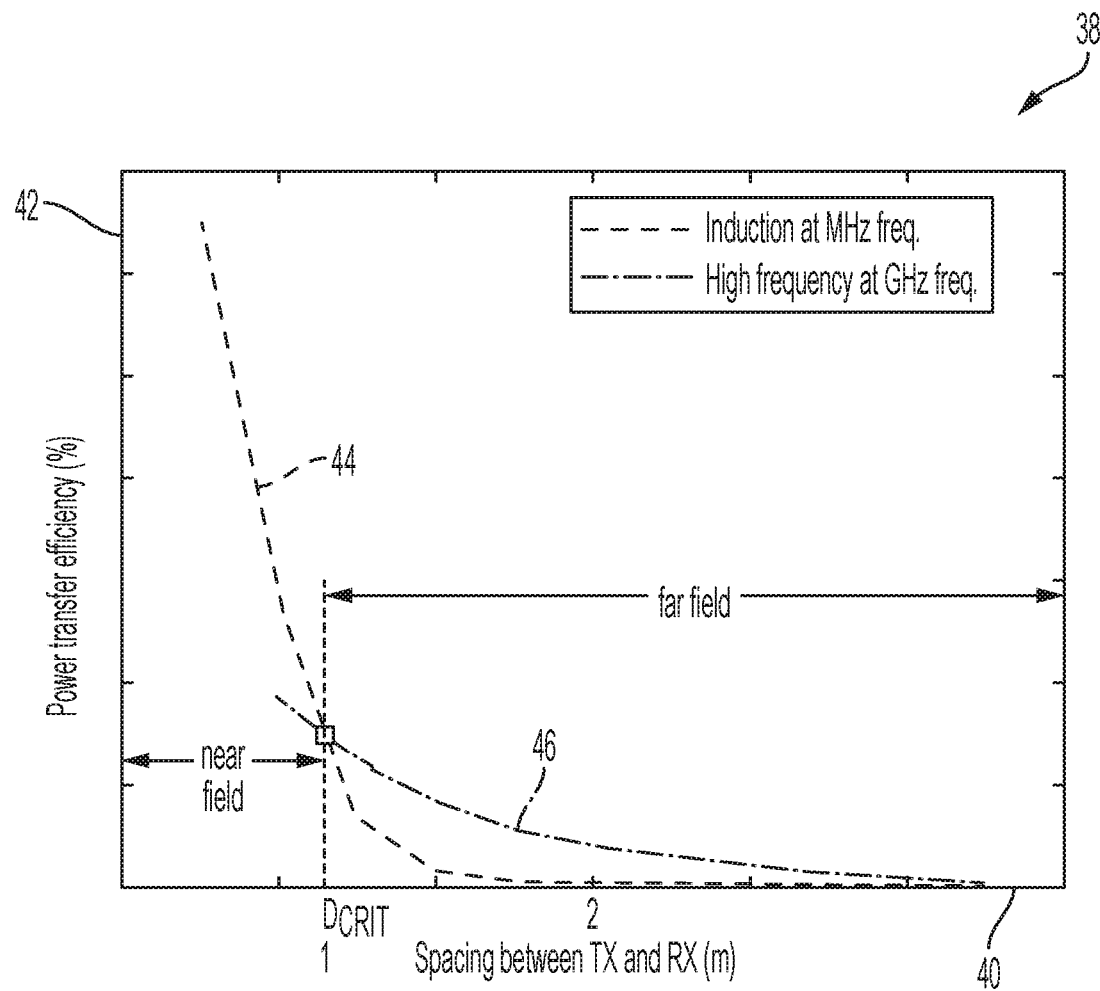
FIG. 3 is a graph of power transfer efficiency vs. separation distance between transmission and reception antennae or inductive coils

FIG. 3 is a graph of power transfer efficiency vs. separation distance between transmission and reception microwave antennae or inductive coils. In FIG. 3, graph 38 includes horizontal axis 40, vertical axis 42, power transfer efficiency/separation-distance between microwave antenna or inductive coils relations 44 and 46. Horizontal axis 40 is indicative of separation distance, in units of meters (m), between transmission and reception antenna or inductive coils used for wireless power transfer. Vertical axis 42 is indicative of power transfer efficiency in units of percent (%).

Power transfer efficiency/separation-distance between inductive coils 44 corresponds to efficiency of wireless power transfer from inductive coil 28 of external interface system 14 to inductive coil 18 of implantable wireless device 10 (as depicted in FIGS. 1-2B). Such wireless power transfer is performed by providing an AC current through inductive coil 28 of external interface system 14, thereby generating an electromagnetic field. The generated electromagnetic field then induces an AC current into inductive coil 18 of implantable biomedical device 10. For graph 38, the frequency of the AC current used for wireless power transfer via inductive coils 18 and 28 can be between 1 and 20 MHz, for example. As shown in graph 38, the efficiency of such wireless power transfer, using inductive coils 18 and 28, rapidly decreases in response to increasing the separation distance between inductive coils 18 and 28. Wireless power transfer using inductive coils 18 and 28 is generally efficient for near-field transmissions. Near-field transmissions are performed when the separation distance between antennae or inductive coils are within a few wavelengths of the transmitted electromagnetic wave. For example, if the largest dimension of a microwave antenna is 10 cm and the frequency of excitation is 5 GHz, then transmissions with separation distances of less than 33 cm are near-field transmissions.

Power transfer efficiency/separation-distance between microwave antennae 46 corresponds to efficiency of wireless power transfer from microwave antenna 30 of external interface system 14 to microwave antenna 20 of implantable wireless device 10 (as depicted in FIGS. 1-2B). Such wireless power transfer is performed by providing an AC current through microwave antenna 30 of external interface system 14, thereby generating an electromagnetic field. The generated electromagnetic field then induces an AC current into microwave antenna 20 of implantable biomedical device 10. As shown in graph 38, the efficiency of such wireless power transfer, using microwave antennae 20 and 30, decreases in response to increasing the separation distance between microwave antennae 20 and 30, but not as rapidly as the rapid decrease of efficiency of wireless power transfer using inductive coils 18 and 28.

As indicated in graph 38, the efficiency of wireless power transfer using inductive coils 18 and 28 is greater than the efficiency of wireless power transfer using microwave antennae 20 and 30, for separation distances less than a critical separation distance $D_{CRIT}$ (e.g., 1 m for the specific embodiment reflected by graph 38). Conversely, for separation distances greater than critical implant depth $D_{CRIT}$, the efficiency of wireless power transfer using microwave antennae 20 and 30 is greater than the efficiency of power transfer using inductive coils 18 and 28. Thus, implantable biomedical device 10 and external interface system 14 can be configured to use inductive coils 18 and 28 and/or microwave antennae 20 and 30 for wireless power transfer.

For example, implantable biomedical device 10 and external interface system 14 can be configured to use inductive coils 18 and 28 for wireless power transfer, in response to a determination that such use in more efficient that a wireless power transfer efficiency when using microwave antennae 20 and 30. Implantable biomedical device 10 and external interface system 14 can be further configured to use microwave antennae 20 and 30 for wireless power transfer, in response to a determination that such use in more efficient that a wireless power transfer efficiency when using inductive coils 18 and 28. Communications between external interface system 14 and implantable biomedical device 10 can be performed concurrently with wireless power transfer using whichever of inductive coils 18 and 28 or microwave antennae 20 and 30 that are not being used for wireless power transfer. Using two antennae (i.e., an inductive coil and a microwave antenna) aligned with one another and configured to operate at such dissimilar frequencies can provide efficient wireless power transfer over many implant conditions (e.g., implant depths $D_{IMPLANT}$, and intervening tissue conditions). Furthermore, inductive coils 18 and 28 and microwave antenna 20 and 30 can be simultaneously used to provide wireless power transfer. In such a configuration, efficient power transfer can be provided without regard to determination of which of inductive coils 18 and 28 or microwave antennae 20 and 30 are more efficient.

Wireless power transfer can be more efficient using far-field transmission by microwave antennae 20 and 30 when the separation distances between implantable biomedical device 12 and interface system 14 exceeds a critical distance. Such dual means of wireless power transfer (i.e., near-field transmissions using inductive coils 19 and 28, and far-field transmissions using microwave antennae 20 and 30) can advantageously permit a patient, who is sitting in one room, to recharge an implantable biomedical device from an interface system located in an adjacent room using far-field transmission, for example. In other embodiments, a dual-channel electronic device can receive operating power and/or recharging power in far-field conditions from remote power sources. In some embodiments, such an electronic device can tune the microwave antenna to frequencies of energy sensed in the environment. The electronic device can scavenge the energy in the environment to provide operating power and/or recharging power. In some embodiments, an interface system for the electronic device can provide and/or direct an electromagnetic transmission to the electronic device. Such reception of energy can minimize discharge of a battery, for example, between near-field recharging events.

Figures 4A, 4B:
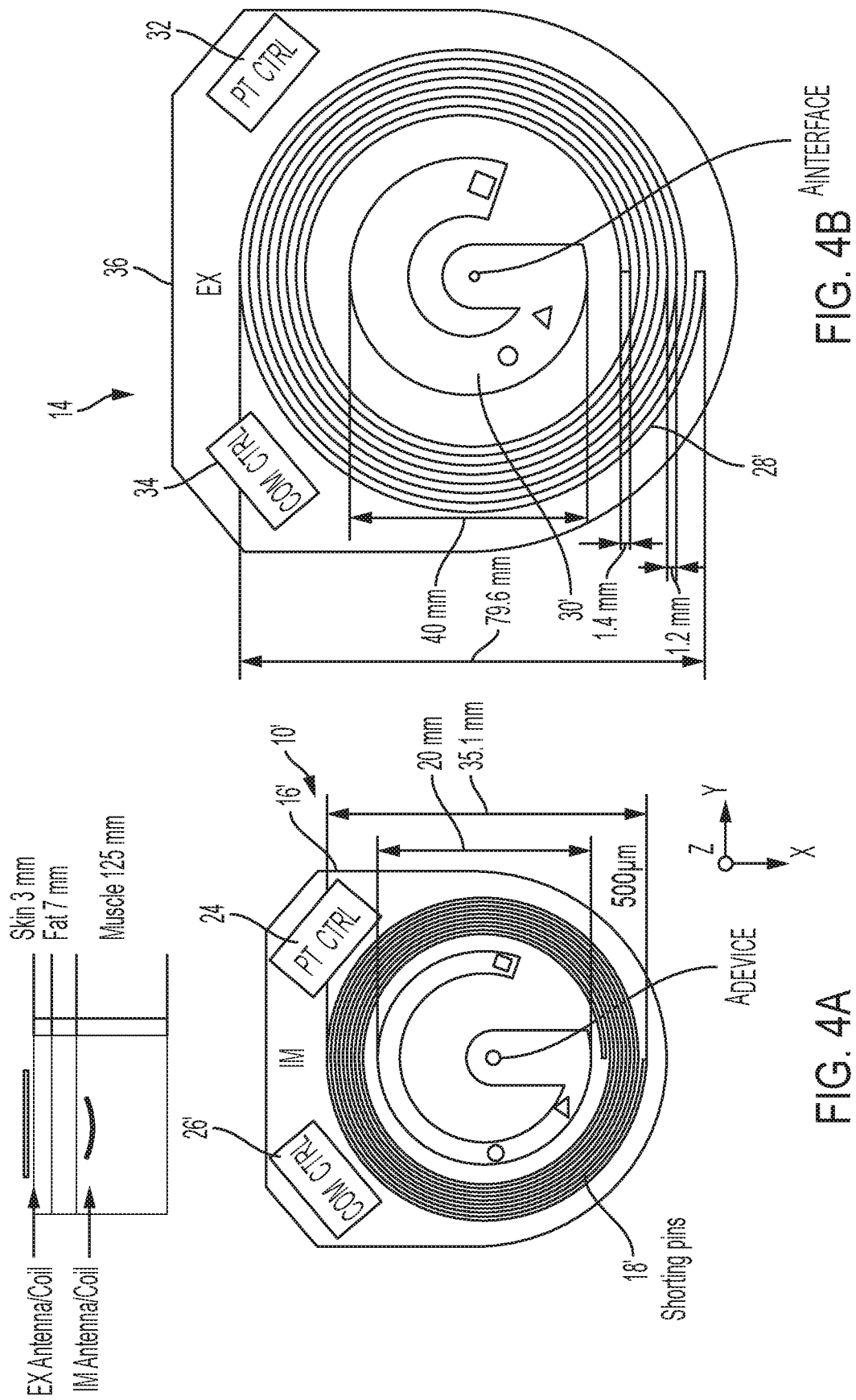
FIGS. 4A-4B are plan views showing another embodiment of inductive coils and microwave antennae for an implantable biomedical device and an external interface system for the implantable biomedical device, respectively.

FIGS. 4A-4B are plan views showing another embodiment of inductive coils and microwave antennae for an implantable biomedical device and an external interface system for the implantable biomedical device, respectively. In FIG. 4A, implantable biomedical device 10' includes inductive coil 18', microwave antenna 20', power-receive controller 24, and communications controller 26. In the depicted embodiment, inductive coil 18' is a microstrip type of structure that has been formed on insulative substrate 16'. Similarly, microwave antenna 20' is also of the microstrip type of structure that has been formed on insulative substrate 16'. Both inductive coil 18' and microwave antenna 20' are centered about central axis $A_{DEVICE}$, such that inductive coil 18' circumscribes microwave antenna 20'. Power-receive controller 24 is configured to provide regulated power to biomedical implantable device 10' using electrical energy coupled into the inductive coil by external interface system 14' for biomedical implantable device 10'. Communications controller 26 is configured to facilitate communications between biomedical implantable device 10 and external interface system 14' for biomedical implantable device 10'.

In FIG. 2B, external interface system 14' includes inductive coil 28', microwave antenna 30', power-transmit controller 32, and communications controller 34. In the depicted embodiment, inductive coil 28' is a microstrip type of structure that has been formed on insulative substrate 36'. Similarly, microwave antenna 30' is also of the microstrip type of structure that has been formed on insulative substrate 36'. Both inductive coil 28' and microwave antenna 30' are centered about central axis $A_{INTERFACE}$, such that inductive coil 28' circumscribes microwave antenna 30'. Power-receive controller 32 is configured to provide an AC current signal in inductive coil 28' so as to excite inductive coil 28' and to transmit wireless power to biomedical implantable device 10'. Communications controller 34 is configured to facilitate communications between biomedical implantable device 10' and external interface system 14' for biomedical implantable device 10'.

Microwave antennae 20' and 30' are G-shaped hybrid coil type antennae. Such G-shaped antennae have resonant frequencies that can be configured by location of an electrical connection to a ground reference. In the FIGS. 4A-4B depictions, three such locations are identified by the triangle Δ, circle ○, and square □ symbols. If the grounding location is at the location represented by the triangle symbol Δ, the resonant frequencies of both microwave antennae 20' and 30' will be approximately 1300 MHz. If the grounding location is at the location represented by the circle symbol ○, the resonant frequencies of both microwave antennae 20' and 30' will be approximately 905 MHz. And ff the grounding location is at the location represented by the circle square □, the resonant frequencies of both microwave antennae 20' and 30' will be approximately 415 MHz. Thus, such a G-shaped hybrid coil type antenna can be configurable to operate at various frequencies.

The frequencies to which microwave antennae 20' and 30' can be configured can be fixed (e.g., by a grounding pin configured to short the G-shaped microwave antenna to a grounding plate), or programmable (e.g., by a switch network configured to selectably short the G-shaped antenna at one of various grounding locations). Such controllable resonant frequency can provide further flexibility to both communications between external interface system 14' and implantable biomedical device 10', and wireless power transfer from external interface system 14 to implantable biomedical device 10'. Such wireless power transfer can be performed using microwave antennae 20' configured to operate at any of the resonant frequencies, to which external interface system 14' and implantable biomedical device 10' can be configured, as well as using inductive coils 18' and 28'. Similarly, such a switch network can be configured to shorten inductive coils 18' and/or 28' so as to change the operation parameters of power transfer and or communications therebetween.

FIGS. 5A-5B are block diagrams of the implantable device and the interface for the implantable device, respectively. In FIG. 5A, implantable biomedical device 10 includes inductive coil 18, microwave antenna 20, power-receive controller 24, communications controller 26, microprocessor 48, memory 50, biomedical device controller 52, and battery 54. Microprocessor 48 is configured receive program instructions from memory 50. Microprocessor 48 can be configured to communicate with each of power-receive controller 24, communications controller 26, and biomedical device controller 52. For example, microprocessor 48 can be configured to receive, from power-receive controller 24, a signal indicative of magnitude(s) of energy induced into inductive coil 18 and/or microwave antenna 20. Microprocessor can communicate then send such signals indicative of magnitude(s) of energy induced into inductive coil 18 and/or microwave antenna 20 to communications controller 26 to be communicated to external interface system 14. External interface 14 can use this information regarding the magnitudes(s) of energy induced into inductive coil 18 and/or microwave antenna 20 to configure external interface system 14 and implantable biomedical device 10 for wireless power transfer and/or communication configuration (e.g., resonant frequency).

Microprocessor 48 can also be configured to receive, from communication controller 26, signals indicative of communications received from external interface system 14, via inductive coil 18 and/or microwave antenna 20. Such signals could be indicative of commands, configurations, and/or requests for data, for example. Such data requests can be for biomedical data obtained by biomedical device controller 52 and/or device data indicative of condition and/or status of various components of implantable biomedical device 10. Microprocessor 48 can then send a command signal(s) to power-receive controller 24, in response to a configuration signal received from external interface system 14, that configures power-receive controller. For example, power-receive controller can be configured to provide regulated power to implantable biomedical device using inductive coil 18 and/or microwave antenna 20. Power-receive controller can then provide regulated power to implantable biomedical device 10. In the depicted embodiment, power-receive controller can be configured to recharge battery 54, for example. In battery-less embodiments, power-receive controller can be configured to provide operating power for implantable biomedical device 10. Microprocessor 48 can also be configured to send and/or receive signals from biomedical controller. For example, microprocessor 48 can send command signals to and/or receive biomedical data signals from biomedical device controller 52.

Microprocessor 48, in some embodiments, can be configured to implement functionality and/or process instructions for execution within implantable biomedical device 10. For instance, microprocessor 48 can be capable of processing instructions stored in memory 50. Examples of microprocessor 48 can include any one or more of a microprocessor, a controller, a digital signal processor(s) (DSP), an application specific integrated circuit (ASIC), a field-programmable gate array (FPGA), or other equivalent discrete or integrated logic circuitry.

Memory 50 can be configured to store information within implantable biomedical device 10 during operation. Memory 50, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 50 is a temporary memory, meaning that a primary purpose of memory 50 is not long-term storage. Memory 50, in some examples, is described as volatile memory, meaning that memory 50 do not maintain stored contents when power to implantable biomedical device 10 is turned off. Examples of volatile memories can include random access memories (RAM), dynamic random-access memories (DRAM), static random access memories (SRAM), and other forms of volatile memories. In some examples, memory 50 is used to store program instructions for execution by microprocessor 48. Memory 50, in one example, is used by software or applications running on implantable biomedical device 10 (e.g., a software program pacing heart rate of a patient) to temporarily store information during program execution.

Memory 50, in some examples, can also include one or more computer-readable storage media. Memory 50 can be configured to store larger amounts of information than volatile memory. Memory 50 can further be configured for long-term storage of information. In some examples, memory 50 include non-volatile storage elements. Examples of such non-volatile storage elements can include magnetic hard discs, optical discs, flash memories, or forms of electrically programmable memories (EPROM) or electrically erasable and programmable (EEPROM) memories.

In FIG. 5B, external interface system 14 includes inductive coil 28, microwave antenna 30, power-transmit controller 32, communications controller 34, microprocessor 56, memory 58, and input/output interface 60. Microprocessor 56 is configured receive program instructions from memory 58. Microprocessor 56 can be configured to communicate with each of power-transmit controller 32, communications controller 34, and input/output interface 60. For example, microprocessor 56 can be configured to send, to power-transmit controller 24, a command signal to provide an AC signal to inductive coil 28 and/or microwave antenna 30. Microprocessor 56 can then a signal from communications controller 34, sent by implantable biomedical device 10, indicative of energy induced into inductive coil 18 and/or microwave antenna. Microprocessor 56 can then configure external interface system for wireless power transfer and send a signal indicative of such configuration to implantable biomedical device 10, so that implantable biomedical device 10 can configure itself accordingly.

Microprocessor 56 can also be configured to receive, from communication controller 26, signals indicative of communications received from implantable biomedical device 10, via inductive coil 28 and/or microwave antenna 30. Such signals could be responsive to commands, configurations, and/or data requests, for example. For example, such data requests can be for biomedical data obtained by biomedical device controller 52 and/or device data indicative of condition and/or status of various components of external interface system 14. Microprocessor 56 can also be configured to send and/or receive signals from input/output interface, which can by a communications interface and/or a user interface, for example.

Microprocessor 56, in some embodiments, can be configured to implement functionality and/or process instructions for execution within external interface system 14. For instance, microprocessor 56 can be capable of processing instructions stored in memory 58. Examples of microprocessor 56 can include any one or more of a microprocessor, a controller, a digital signal processor(s) (DSP), an application specific integrated circuit (ASIC), a field-programmable gate array (FPGA), or other equivalent discrete or integrated logic circuitry.

Memory 58 can be configured to store information within external interface system 14 during operation. Memory 58, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 58 is a temporary memory, meaning that a primary purpose of memory 58 is not long-term storage. Memory 58, in some examples, is described as volatile memory, meaning that memory 58 do not maintain stored contents when power to external interface system 14 is turned off. Examples of volatile memories can include random access memories (RAM), dynamic random-access memories (DRAM), static random access memories (SRAM), and other forms of volatile memories. In some examples, memory 58 is used to store program instructions for execution by microprocessor 56. Memory 58, in one example, is used by software or applications running on external interface system 14 (e.g., a software program pacing heart rate of a patient) to temporarily store information during program execution.

Memory 58, in some examples, can also include one or more computer-readable storage media. Memory 58 can be configured to store larger amounts of information than volatile memory. Memory 58 can further be configured for long-term storage of information. In some examples, memory 58 include non-volatile storage elements. Examples of such non-volatile storage elements can include magnetic hard discs, optical discs, flash memories, or forms of electrically programmable memories (EPROM) or electrically erasable and programmable (EEPROM) memories.

Figure 6:
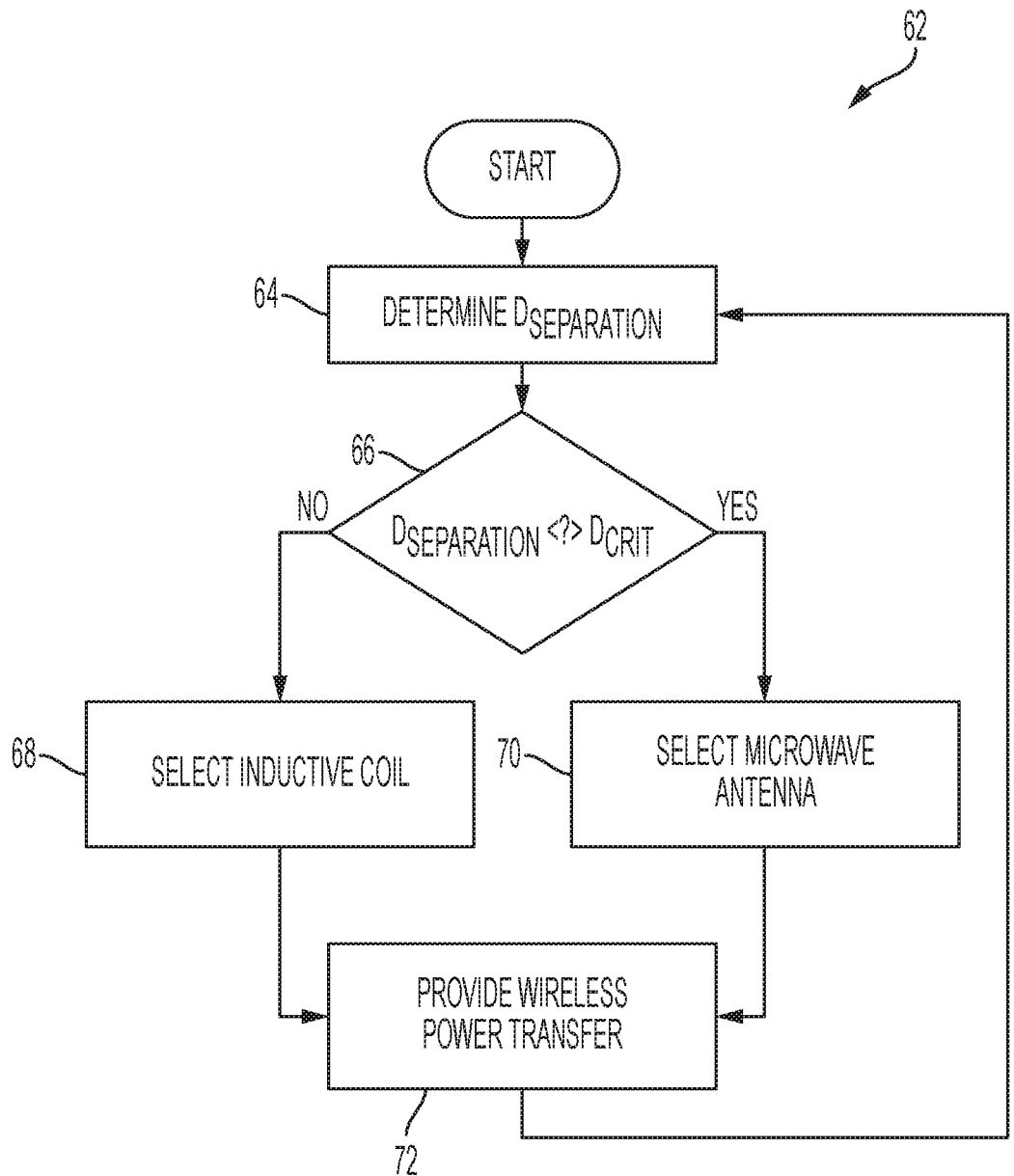
FIG. 6 is a flow chart of a method for providing wireless power transfer to a dual-channel electronic device.

FIG. 6 is a flow chart of a method for providing wireless power transfer to a dual-channel electronic device. In FIG. 6, method 62 begins at step 64, where a separation distance $D_{SEPARATION}$ between a dual-channel electronic device and an interface system for the dual-channel electronic device is determined. Then, at step 66, the separation distance $D_{SEPARATION}$ determined is compared with a critical separation distance $D_{CRIT}$. If the critical separation distance $D_{CRIT}$ is greater than the separation distance $D_{SEPARATION}$ determined, the method proceeds to step 68, where and inductive coil is selected for providing wireless power transfer. If, however, the separation distance $D_{SEPARATION}$ determined is greater than the critical separation distance $D_{CRIT}$, the method proceeds to step 70, where a microwave antenna is selected for providing wireless power transfer. Then, at step 72, the wireless power transfer is provided to the dual-channel electronic device using either the selected inductive coil or the selected microwave antenna according to the comparison at step 66. The method then returns to step 64 where the separation distance $D_{SEPARATION}$ between a dual-channel electronic device and an interface system for the dual-channel electronic device is again determined. The frequency of such determination of separation distance can be such that wireless power transfer is maintained in a fashion with little interruption.

Various ways for calculating the critical separation distance $D_{CRIT}$ can be used. For example, a calibration step can be performed in which the separation distance between the interface system and the dual-channel electronic component is varied. At each separation distance exercised during such a calibration step, the various antennae can be excited using various frequencies and amplitudes of excitation. Wireless power transfer efficiency can be measured for each of the tested conditions. The critical separation distance $D_{CRIT}$ can be calculated, for example, as the separation distance at which power transfer efficiency is substantially equal using each of the inductive coil and the microwave antenna.

In some embodiments, instead of determining the separation distance and comparing the separation distance determined with a critical separation distance, selection of the microwave antenna and/or the inductive coil is determined in other ways. For example, in some embodiments, the strength of the signals induced in microwave antenna and the inductive coil are compared with one another. Based on this comparison, the microwave antenna and/or the inductive coil is used for wireless power transfer. For example, if the strength of the signal induced in the microwave antenna is greater than the strength of the signal induced in the inductive coil, then the power transfer or power receive controller can select the microwave antenna for wireless power transfer. In other embodiments, the interface system can send a signal to the dual-channel electronic device, the signal being indicative of which of the microwave antenna or inductive coil will be used for wireless power transfer. In some embodiments, the transmitting microwave antenna can be used to transmit signals at various frequencies. The strengths of these signals of various frequencies, which are induced in the receiving microwave antenna, can also be compared so as to determine an optimal frequency for wireless power transfer.

In some embodiments, microwave antenna and/or inductive coil for wireless power transfer can be selected based on measurements of power transfer efficiencies. For example, a first power transfer efficiency corresponding to wireless power transfer using the inductive coils can be measured. A second power transfer efficiency corresponding to wireless power transfer using the microwave antenna can be measured. The first and second power transfer efficiencies can be compared, and the inductive coil and/or the microwave antenna for wireless power transfer can be selected based on this comparison. In some embodiments, the measurement and comparison of first and second power transfer efficiencies can be performed at various time intervals. Such scheduled comparisons can facilitate frequent selection of means for wireless power transfer, so that efficient power transfer is regularly ensured. A table and/or graph of power transfer efficiencies vs. frequencies can be maintained. This table can be used for selection of the antenna and/or frequency to be used for wireless power transfer.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A dual-channel electronic device comprising:
an inductive coil centered about a central axis;
a power-receive controller configured to provide regulated power to the dual-channel electronic device using electrical energy coupled into the inductive coil by an interface system for the dual-channel electronic device;
a microwave antenna centered about the central axis; and
a communications controller configured to facilitate communications between the dual-channel electronic device and the interface system for the dual-channel electronic device, wherein the electrical energy coupled into the inductive coil is of a first frequency used for near-field operation, the first frequency different than a second frequency of signals received via the microwave antenna, the second frequency used for far-field operation.

2. The dual-channel electronic device, wherein the dual-channel electronic device is a biomedical implantable device.

3. The dual-channel electronic device of claim 1, further comprising:
a battery,
wherein the power-receive controller is a battery controller configured to recharge the battery using electrical energy coupled into the inductive coil by an interface system for the dual-channel electronic device.

4. The dual-channel electronic device of claim 3, wherein the battery controller is further configured to determine to which of the inductive coil or the microwave antenna is the interface system using to wirelessly transfer power.

5. The dual-channel electronic device of claim 3, wherein the battery controller is further configured to charge the battery simultaneously using both the energy induced in the inductive coil and in the microwave antenna.

6. The dual-channel electronic device of claim 1, wherein the battery controller is further configured to recharge the battery using electrical energy coupled into the microwave antenna by an interface system for the dual-channel electronic device.

7. The dual-channel electronic device of claim 1, wherein the inductive coil is formed by a spiral-patterned conductive layer on the insulative substrate, the inductive coil extending from an inner radial dimension, as measured from the central axis, to an outer radial dimension, as measured from the central axis, and wherein the microwave antenna is formed by antenna-patterned conductive layer on the insulative substrate, the microwave antenna having an outer radial dimension, as measured from the central axis, that is less than the inner radial dimension of the inductive coil.

8. The dual-channel electronic device of claim 7, further comprising:

a switch network having a plurality of switches, each configured to provide electrical connection between the microwave antenna and the ground plane at a corresponding location, wherein the communication controller is configured to control the resonance frequency of the microwave antenna by controlling a switch network.

9. The dual-channel electronic device of claim 1, wherein the microwave antenna has a resonance frequency that is configured by location of an electrical connection to a ground plane.

10. The dual-channel electronic device of claim 9, wherein the communications controller is configured to control the resonant frequency based on a determination of strength of signals received from the interface system for the dual-channel electronic device.

11. The dual-channel electronic device of claim 1, wherein the microwave antenna is a G-shaped antenna.

12. The dual-channel electronic device of claim 1, wherein the microwave antenna is a split shell antenna.

13. An external interface system for a dual-channel electronic device comprising:

an inductive coil centered about a central axis;

a power-transmit controller configured to excite the inductive coil at a first frequency used for near-field operation so as to transmit wireless power to the dual-channel electronic device;

a microwave antenna centered about the central axis;

a communications controller configured to facilitate communications between the dual-channel electronic device and the interface system for the dual-channel electronic device, wherein the communications are conducted via signals of a second frequency used for far-field operation, the second frequency different than the first frequency, the communications transmitted and/or received via the microwave antenna.

14. The interface system of claim 13, wherein the power-transmit controller is further configured to excite the microwave antenna so as to transfer wireless power to the dual-channel electronic device.

15. The interface system of claim 14, wherein the power-transmit controller is further configured to determine which of the inductive coil or the microwave antenna to excite for transferring wireless power to the dual-channel electronic device.

16. The interface system of claim 13, wherein the inductive coil is formed by a spiral-patterned conductive layer on the insulative substrate, the inductive coil extending from an inner radial dimension, as measured from the central axis, to an outer radial dimension, as measured from the central axis, and wherein the microwave antenna is formed by antenna-patterned conductive layer on the insulative substrate, the microwave antenna having an outer radial dimension, as measured from the central axis, that is less than the inner radial dimension of the inductive coil.

17. The interface system of claim 13, wherein the microwave antenna has a resonance frequency that is configured by location of an electrical connection to a ground plane.

18. The interface system of claim 17, further comprising:

a switch network having a plurality of switches, each configured to provide electrical connection between the microwave antenna and the ground plane at a corresponding location, wherein the communication controller is configured to control the resonance frequency of the microwave antenna by controlling a switch network.

19. A method for supplying energy to a dual-channel electronic device, the method comprising:

determining a separation distance between the dual-channel electronic device and an interface system for providing wireless power transfer to the dual-channel electronic device;

comparing the separation distance determined with a critical separation distance;

selecting, based on the comparison of the separation distance with the critical separation distance, an inductive coil or a microwave antenna for provision of wireless power transfer; and providing wireless power transfer to the dual-channel electronic device using the inductive coil via a signal of a first frequency used for near-field operation or the microwave antenna selected via a signal of a second frequency used for far-field operation, the second frequency different than the first frequency.

20. The method of claim 19 further comprising:

wherein the inductive coil is selected to provide wireless power transfer if the separation distance determined is greater than the critical separation distance, and wherein the microwave antenna is selected to provide wireless power transfer if the critical separation distance is greater than the separation distance determined.

* * * * *